United States Patent [19]
Fombon

[11] Patent Number: 5,288,388
[45] Date of Patent: Feb. 22, 1994

[54] HOMOGENEOUS POTENTIOMETER SENSOR

[75] Inventor: Jean-Jacques Fombon, Meyzieu, France

[73] Assignee: Societe Anonyme: Societe Lyonnaise d'Electronique Appliquee, France

[21] Appl. No.: 280,494

[22] Filed: Dec. 6, 1988

[30] Foreign Application Priority Data

Dec. 9, 1987 [FR] France ............... 87 17437

[51] Int. Cl.⁵ .................................... G01N 27/414
[52] U.S. Cl. ............................. 204/416; 204/418
[58] Field of Search ............ 204/416, 418, 419, 420, 204/435

[56] References Cited

U.S. PATENT DOCUMENTS

| | | | |
|---|---|---|---|
| 2,508,171 | 5/1950 | Kaufman | 204/197 |
| 3,607,710 | 9/1971 | Farren | 204/419 |
| 3,700,577 | 10/1972 | Grauer | 204/435 |
| 3,755,125 | 8/1973 | Shaw et al. | 204/415 |
| 3,856,649 | 12/1974 | Genshaw et al. | 204/435 |
| 3,929,588 | 12/1975 | Parker et al. | 204/415 |
| 4,020,830 | 5/1977 | Johnson et al. | 204/418 |
| 4,052,285 | 10/1977 | Dobson | 204/419 |
| 4,062,750 | 12/1977 | Butler | 204/403 |
| 4,133,732 | 1/1979 | Boeke | 204/435 |
| 4,235,687 | 11/1980 | Romette et al. | 204/416 |
| 4,556,474 | 12/1985 | Pierson | 204/416 |
| 4,582,589 | 4/1986 | Ushizawa et al. | 204/418 |

FOREIGN PATENT DOCUMENTS 492936 9/1938 United Kingdom ............... 204/420

OTHER PUBLICATIONS

Patent Abstracts of Japan, vol. 8, No. 215 (P-305) [1652], Oct. 2, 1984.

*Primary Examiner*—T. Tung
*Attorney, Agent, or Firm*—Bacon & Thomas

[57] ABSTRACT

The invention relates to measuring the concentration of ions in a medium. The potentiometric sensor of the invention comprises a body (7) in the form of a matrix body made of a single type of material which does not conduct electricity, which is chemically inert, and which is suitable for being filled with various materials in the dispersed, the dissolved, or the grafted state. A sensitive zone of the matrix body comprises a layer or thickness (9) of an ionically conductive material for being put into contact with the measurement solution, an underlayer or thickness (10) of an electronically conductive material, and an intermediate layer or thickness (11) providing intimate connection between said layer (9) and said underlayer (10). A conductor (12) passes through a portion of the matrix body (7) in sealed manner and is inserted into the underlayer (10). The sensor is particularly applicable to measuring biological fluids.

18 Claims, 5 Drawing Sheets

HOMOGENEOUS POTENTIOMETER SENSOR

The present invention relates to the technical field of determining or measuring activity or ion concentration in a medium, and it relates more particularly to probes generally referred to as potentiometic sensors or as selective electrodes.

BACKGROUND OF THE INVENTION

Figure 1:
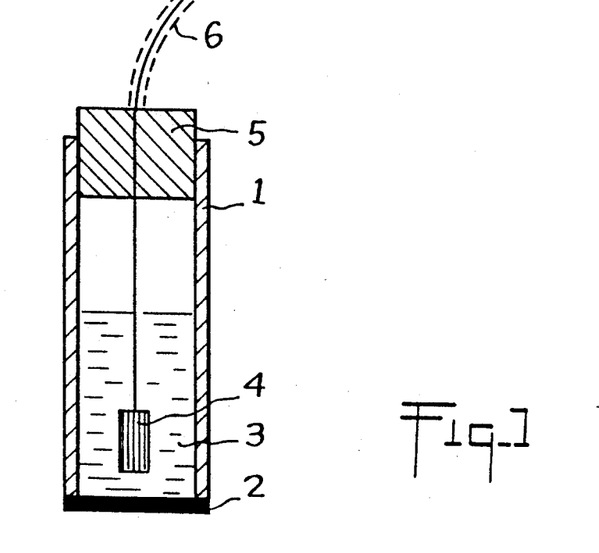
FIG. 1 is a diagrammatic elevation in section through a prior art electrode.

Present selective electrodes having an organic membrane are used, in particular, for measuring the following cations: hydrogen; sodium; potassium; calcium; lithium; magnesium; and barium; or the following anions: nitrate; fluoborate; chloride; and carbonate. They are applied, for example, to measuring the concentrations of some of these ions in biological fluids (blood, serum, plasma, urine). They are generally constituted by five essential parts shown in FIG. 1 which is a diagram illustrating the prior art:

- an electrode body 1 generally constituted by a tube of polymer that does not conduct electricity;
- a sensitive membrane 2 constituted by a dispersion of a sensitive ion-conducting material optionally together with a conducting salt in a thin film which is generally constituted by polyvinyl chloride including a plasticizer;
- an internal solution 3 which may optionally be gelled, containing a known constant concentration of the ion to which the electrode is sensitive, and generally also a known constant concentration of chloride ions;
- an internal reference element 4 generally constituted by a piece of silver coated with silver chloride and immersed in the internal solution 3; and
- an electrode head 5 for passing a screened connection cable 6 or equipped with a connector enabling such a cable to be connected thereto.

Such selective electrodes of a design which is now conventional are made using a technology which is difficult and expensive to implement but which is suitable for satisfying an important constraint, namely that the various different materials must be suitable for being assembled together even though at least some of them are in the presence of a saline aqueous solution. The assembly must conserve effective sealing throughout the lifetime of the electrode under various environmental conditions.

Further, these electrodes are rather fragile and their shape as well as their positioning in use cannot be selected freely by the manufacturer or by the user.

Getting rid of the internal gell or solution and the reference element would naturally represent a considerable simplification. Unfortunately, electrochemists are aware that a direct metallic contact on the rear face of the sensitive membrane is not feasible when the charges moving through the membrane are constituted solely by ions. In this case the transfer of charge between ions and electrons is poorly defined since there is no stable oxydo-reducing system at the interface, with the interface, in addition, presenting a sharp phase transition of uncertain geometry. This difficulty is also encountered with glass membrane pH measuring electrodes for which an internal solution and reference element continue to be universely employed.

Several authors have described selective electrodes in which solid contacts are used. In this context, reference may be made to the excellent bibliography of B.P. Nikolskii and E.A. Materova in "Solid-contact in membrane ion selective electrodes" published in "Ion Selective Electrodes Review", 1985, vol. 7, pp. 3-39, which brings together the descriptions and the results which have been obtained.

Some publications or inventions mention electrodes making use of an intimate mixture of an ionic conductor and of an electronic conductor or an oxydo-reducing equilibrium in a polymer membrane. Mention may be made in this context of Russian patent number 898314 (1981). Solid contact electrodes based on the use of carbon have also been described, in particular by D. Midgley and D.E. Mulcaby in "Carbon substrate electrode" published in "Ion Selective Electrode Reviews" vol. 5, no. 2, 1983, pp. 165-241. It appears that such systems should be rejected because they give rise to interference from the oxydo-reducing species present in the measurement solutions.

The use of silicone elastomer for constituting a composite electrode has also been mentioned in French patent number 79 28 651 (2 469 202). The "composite electrodes" described in this patent are constituted by dispersions of mixtures of inorganic species distributed in a way which satisfies no precise configuration. Further, none of them makes use of a filler of a species sensitive to ions and having purely ionic conductivity.

Mention may also be made of an article by R.W. Cattrall and I.C. Hamilton published in "Ion Selective Electrodes Review", vol. 6, no. 2, 1984 entitled "Coated wire ion selective electrodes" and relating to selective electrodes comprising a metal support directly coated with a polymer film incorporating an electroactive conductor.

Electrodes of this type are heterogeneous in character and do not give satisfaction because of the sharp and ill-defined transition between two very different solid phases constituted by a noble metal and by a polymer film. This gives rise to instability in electrical continuity at the interface. The same remark applies to French patent number 2 262 302 which describes an electrode based on depositing a membrane of silicone with an ionophore filler directly deposited on a plate of graphite.

Mention may also be made of the constructive proposal made by Jose L.F.C. Lima and Adelio A.S.C. Machado in the publication "Analyst", July 1986, vol. III. In this proposal, a selective electrode is constituted by a membrane of PVC including a filler of a sensitive species and covering a solid support made of conductive epoxy. It appears that such a structure is still not satisfactory because of the large difference in nature between the two solid materials respectively constituting the electronic conductor element and the ionic conductor element, with the result that there is considerable potential drift as indicated in the comparative example which appears in the present patent specification.

Such structures,, likewise heterogeneous in character, also suffer from the problem of sealing which is difficult to solve in the long term.

Finally, ion selective sensors having an inorganic sensitive element of the compressed pellet type and having direct electrical contact, such as those sold by numerous manufacturers, all have combined electrical conduction (i.e. both ionic and electronic) and this gives rise to interference from oxydo-reducing systems.

The present invention seeks to remedy the above drawbacks and proposes a new potentiometic sensor having the advantages of being:

easily made at low cost in any configuration suitable for the intended application;

resistant to physical, thermal, chemical, and mechanical constraints that may be applied to it;

compact;

easily put into place or positioned at will by an operator while a measurement is being performed; and perfectly sealed.

SUMMARY OF THE INVENTION

The present invention provides a homogeneous potentimetric for sensing the presence of ions in a measurement solution, the sensor comprising a body having at least one active surface portion or face delimiting at least one zone which is sensitive to an ionic species, the sensor being provided with a conductor of an electrically conductive material disposed in relationship to the body and connected to an electrical connection cable, wherein:

the body is a matrix body made of a single type of material which does not conduct electricity, which is chemically inert, and which has the ability to be filled with various different materials in the dispersed, dissolved, or grafted state;

the sensitive zone of the matrix body comprises:
a layer or thickness of an ionically conductive material for being put into contact with the measurement solution;
an underlayer or underthickness of an electronically conductive material; and
an intermediate layer or thickness in intimate connection with the layer and with the underlayer; and the conductor passes through a portion of the matrix body in sealed manner and is inserted into the underlayer.

BRIEF DESCRIPTION OF THE DRAWINGS

Embodiments of the invention are described by way of example with reference to the accompanying drawings, in which:

FIG. 11 is an elevation in section of a Lima-Machado electrode used for comparison purposes.

MORE DETAILED DESCRIPTION

Figure 2:
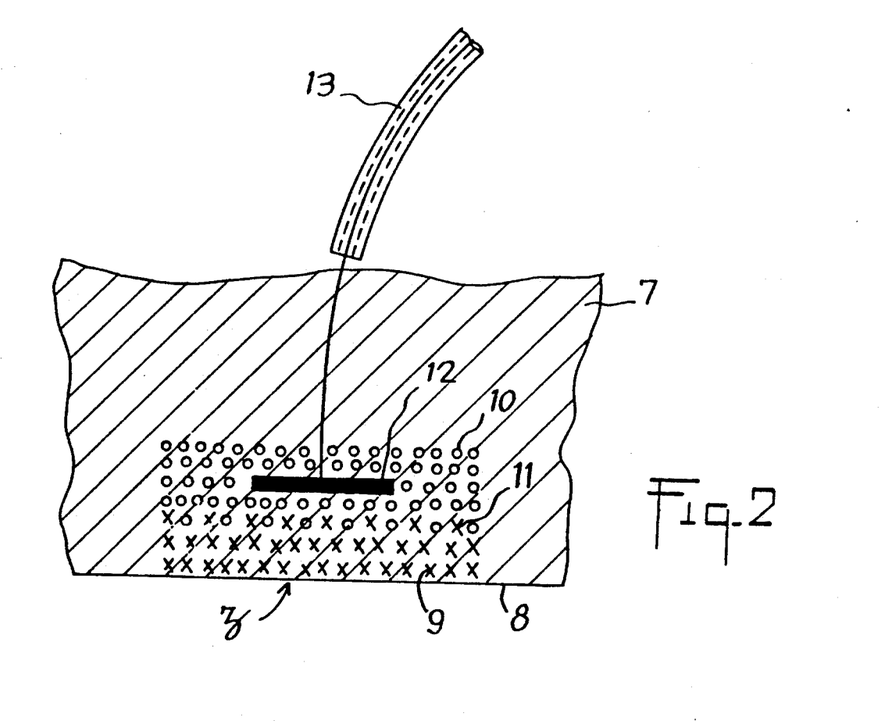
FIG. 2 is a diagrammatic section on a different scale showing the theory of making a novel sensor in accordance with the invention.

In a first embodiment of the invention shown in FIG. 2, the potentiometer sensor comprises a matrix 7 of a material which does not conduct electricity, which is chemically inert, and which is capable of being filled with various different materials in the dissolved or the dispersed state. The material of the matrix 7 may be constituted by a polymer or by an elastomer selected for its suitability for containing one or more fillers which may be dispersed, solid, or liquid. By way of non-limiting example, suitable materials include:

chlorinated compounds;

epoxy compounds;

olefin compounds (polyethylene, polypropylene, silicone elastomers;

fluorosilicone elastomers; and polysiloxanes.

The matrix material which is intended to constitute the body of the sensor is preferably selected from the family of silicone elastomers which have the property of being easily shaped, thereby enabling any simple or multiple geometry to be made easily and cheaply by molding and/or machining, and gluing and/or chemical bonding. Typical geometries include films, sheets, and strips.

These materials are also very inert chemically with respect to acidic or basic aqueous solutions and with respect to most organic solvents.

Close to a zone z of a so-called "active" face 8 of a matrix body 7 and intended to be placed in contact with the measurement solution, the material contains either locally or over its entire area a filler 9 of an ionically conductive material having selective response properties with respect to ions.

The ionically conductive species 9 represented by "x" symbols in the drawings is flush with the face 8 and occupies a thickness lying in the range of a few micrometers to a few millimeters. These species may be associated with an organic salt (not shown) for the purpose of improving the overall conductivity of the sensor, where necessary. Such a salt may be partially disassociated within the inert matrix body. The salt could be sodium tetraphenylborate or potassium tetrakis-(p-chlorophenyl)borate, or any other appropriate compound.

The ionically conductive species or filler 9 which determines the specific character of the sensor may be constituted by one of the ion exchanging organic species already used in current commercial sensors, and selected for compatibility with the matrix material. By way of non-limiting example, mention may be made of various ionophore compounds described by W. Simon in the article "Ion selective electrodes based on neutral carriers" in the work "Ion selective electrodes in Analytical Chemistry" published by H. Freiser, Plenum, 1978, pp. 211–281, e.g. the following compounds known to the person skilled in the art:

for $K^+$ ions : valinomycin;

for $Na^+$ ions : ETH 227;

for $Ca^{++}$ ions : ETH 1001;

for $H^+$ ions : tri-n-dodecylamin for $Li^+$ ions : ETH 149; and for $NH_4^+$: nonactin +monactin.

Other compounds can also be used:

for $NO_3^-$ ions: tridodecylmethyl dibenzylammonium chloride;

for $Ca^{++}$ ions: calcium dioctylphenylphosphate; and for $Na^+$ ions: methylmonensin.

As a sublayer relative to the ionic conductor 9, the inert matrix material 7 contains, likewise in the dispersed state, a filler 10 of an electronically conductive material which is represented in the drawings by "o" symbols.

The filler 10 is intimately connected to the ionically conductive material 9 by an intermediate intimate connection thickness or layer 11, but in all circumstances it remains separated from the active face 8 by the thickness of the filler 9 in order to be protected against coming into contact with the measurement solution. The filler 10 is distributed and enclosed in the matrix material 7 in such a manner as to establish a concentration gradient with the filler 9 in the intermediate layer 11, thereby providing intimate contact and progressive transition between the fillers 9 and 10. The thickness of the filler 10 may lie in the range of a few micrometers to a few millimeters.

The electronic conductor is preferably constituted by a suitable conductive material capable of being reduced to a powder of very small grain size, and preferably with a grain size less of than 5 micrometers. Carbon is quite suitable. Carbon filled silicone elastomers are already well known for their properties of electronic conductivity (resistitivity of less than 5 $\Omega$.an), which means that they are used as anti-static materials in the semiconductor industry.

Equivalently, the electronic conductivity provided by the filler 10 could also be provided by selecting chemical substances which constitute oxydo-reducing systems, e.g. ferrocene-ferricicim dispersed in such a manner as to avoid coming into contact with the measurement solution.

A potentiometric sensor in accordance with the invention also include a conductor 12 providing electrical continuity between the filler 10 and a connection cable 13. The conductor 12 is constituted, for example, by a piece of metal in the form of a plate, a bar, a cylinder, a wire, or the like, which is fixed to the cable 13 and which is embedded in the thickness of the electronically conducting layer 10.

The conductor 12 may be constituted by a conducting piece of metal or by a piece of semiconductor material, preferably silicon. In this case, the conductor 12 is constituted by a monocrystaline plate having its surface coated with an oxide material.

The above-described sensor is characterized by the use of the same type of material as the matrix for all of the components of the sensor and by the absence of any internal liquid solution. This novel structure presents the following advantages:

- effective and long-lasting solution of sealing problems at the interfaces between the various component parts of the sensor;
- intimate connection between the fillers providing a progressive change in contact ensuring charge transfer which is stable and reproducible;
- stable measurements are obtained with a short response time;
- by keeping the electronically conductive filler away from the measurement solution, the redox response is completely absent when the sensitive element is a purely ionic conductor (e.g. ionophore); and
- manufacturing costs are reduced and the sensor may be made in various geometrical shapes including that of a plate, and these two advantages make it possible to envisage manufacturing sensors for one use only which is particularly advantageous in medical applications.

Figure 3:
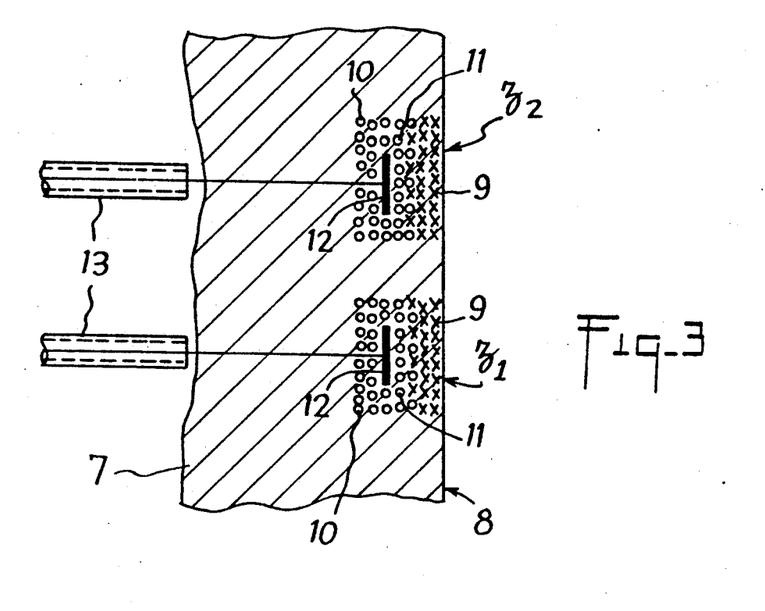
FIG. 3 is a diagrammatic section analogous to FIG. 2, but showing a development thereof.

The new sensor structure of the invention provides multiple possibilities in realization and in application which have never been achieved heretofore. One of these possibilities is that of making a sensor possessing a plurality of sensitive zones $z_1$, $z_2$ which are separate from one another as shown in FIG. 3. The sensitive zones z are made as described above and may have selective sensitivities which are identical or different depending, in particular, on the choice of filler 9. It thus becomes possible to provide a multiple sensor for measuring and correlating measurements of a given chemical species or for providing simultaneous measurements of several different chemical species.

Other possibilities in realization and in application appear from the following examples which also show how the sensor is used.

EXAMPLE 1

A selective electrode for measuring potassium ions was made using the method described below, and illustrated in FIG. 4.

An aluminum alloy mold was used to make a rectangular block of a silicone elastomer sold by Rhome Poulenc under the trademark Rhodorsil, ref. RTV 141, in the form of two liquid components A and B with cross-linking taking place at ambient temperature over a period of 24 hours after mixing. The components A and B were mixed as laid down by the manufacturer and the operating procedure followed the instructions provided for this purpose. The mold was designed to obtain a molded piece 20 constituting the matrix body 7 and having a cylindrical well 21 with a diameter of 5 millimeters and a depth of 5 millimeters.

In addition, a filler 10 was prepared in the form of a dispersion of carbon powder ref. UCP 1M ULTRA F (Ultra Carbon Corporation) at a concentration of 70% by weight in the Rhodorsil A +B elastomer in the liquid monomer state, prepared as above. The mixture obtained was poured into the well 21. After this mass constituting the filler 10 had polymerized, about 1 mg of Rhodorsil mononer was mixed with about 0.05 mg of valinomycine constituting the filler 9 and dissolved in 20 $\mu$l of mesitylen solvent. After being homogenized, this mixture was deposited in the well 21 ensuring that the polymerized carbon-filled mass was completely covered.

After drying and polymerization, the filler 9 lay in the plane of the active face 8 in which it delimited the sensitive zone z. A metal contact 22 was then inserted through the molded piece 20. This contact was connected to a screened cable 23 and was fixed in sealed manner to the matrix substance by a silicone sealing compound sold by Rhone Poulenc under the reference CAF4.

After being made in this way, the selective sensor was immersed for 24 hours in conventional manner in an aqueous solution of $10^{-2}$ mol/l potassium chloride in order to condition it to the chemical species for which it had been selected. A sensor made in this way was then tested in a measurement medium constituted by a solution of 0.1 mol/l, tris-(hydroxymethyl)aminomethane (TRIS) adjusted to a pH of 9 using 1 mol/l HCl and having various concentrations of potassium chloride dissolved therein lying in the range $10^{-5}$ mol/l and $10^{-1}$ mol/l.

The reference electrode used was a standard calomel type electrode (Tacussel, type C8) and it was fitted with an extension filled with a TRIS buffer solution prepared as mentioned above. The measuring apparatus used was a high input impedance ph-meter/millivoltmeter (Tacussel type Minisis 8000) fitted with a potentiometer recorder (Tacussel, type Ecoscript).

Potentials settled down completely after the sensor had been immersed for one minute. The measured values are listed below.

| Concentration of Potassium Ions | Measured Potential |
| --- | --- |
| 0 | −48.7 mV |
| $10^{-5}$ mol/l | −39.5 mV |
| $10^{-4}$ mol/l | +5.5 mV |
| $10^{-3}$ mol/l | +59.8 mV |
| $10^{-2}$ mol/l | +114.8 mV |
| $10^{-1}$ mol/l | +171.3 mv |

EXAMPLE 2

Figure 5:
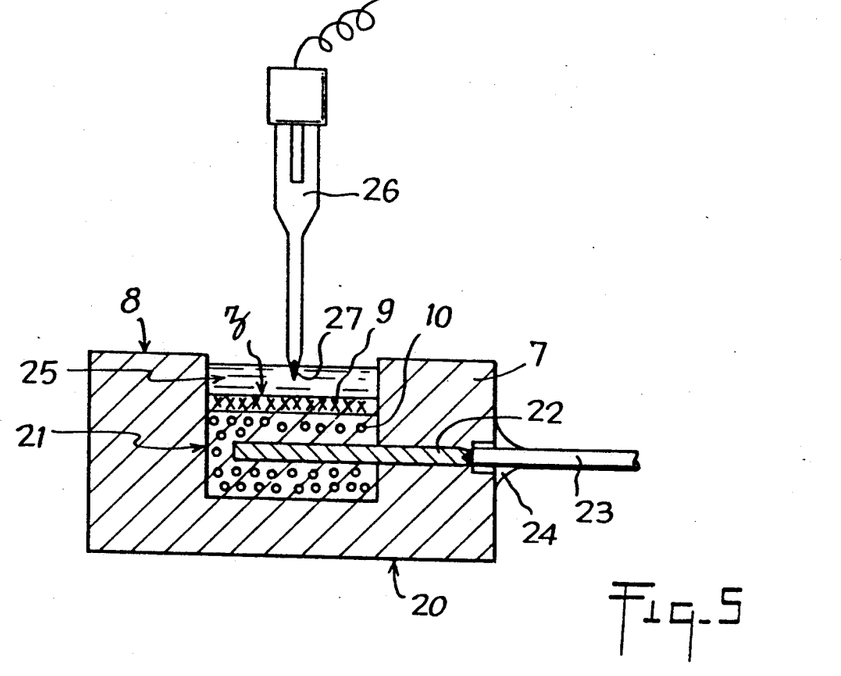

A selective electrode for measuring potassium ions in small sample volumes was made using the method described below and illustrated in FIG. 5.

The sensor was made using the same method as in Example 1, except that the sensitive zone z is set back by about 2 Mm from the active face of the body 20. By setting back the active zone, a small cup 25 is defined suitable for receiving a volume of 20 µl to 50 µl, i.e. a sample of about one drop of the measurement solution.

In such an example, an external reference electrode 26 terminated by a capillary liquid junction 27 is immersed in the solution retained by the cup 25 forming the measurement chamber.

Figure 4:
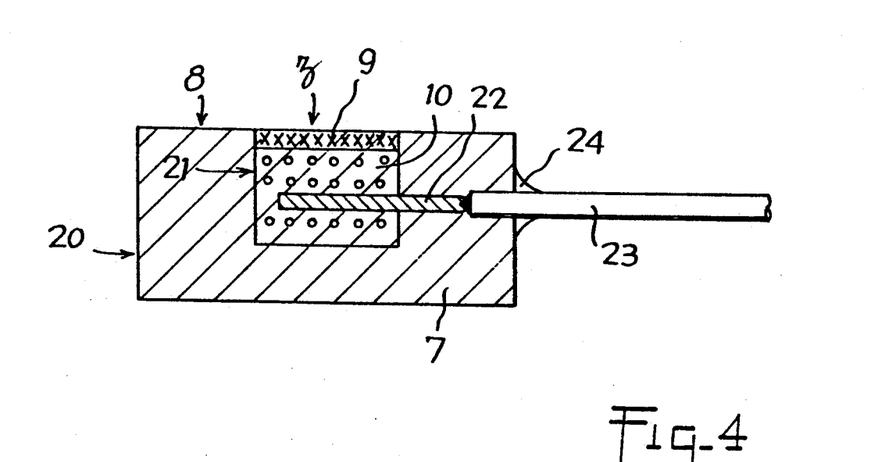
FIGS. 4 to 6 are elevations in section showing variant embodiments of a sensor in accordance with the invention.

The other components of the sensor are identical to those of FIG. 4.

The results obtained with such a configuration of the sensor are listed below.

| Concentration of Potassium Ions (in the presence of $10^{-1}$ mol/l NaCl) | Measured Potential |
| --- | --- |
| $10^{-5}$ mol/l | 122.8 mV |
| $10^{-4}$ mol/l | 149.2 mV |
| $10^{-3}$ mol/l | 208.8 mV |
| $10^{-2}$ mol/l | 263.4 mV |
| $10^{-1}$ mol/l | 320.6 mV |

EXAMPLE 3

Figure 6:
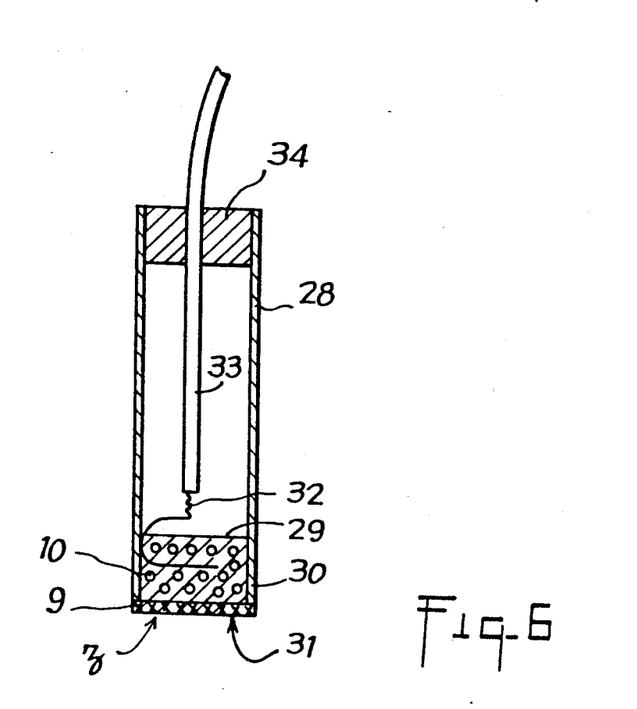

A selective electrode for measuring ammonium ions was made using the method described below (FIG. 6).

A length 28 of about 100 mm was cut from a tube of silicone elastomer having an inside diameter of 8 millimeters and a wall thickness of 2 millimeters. Such a tube is sold by Etablissements Verneret under the reference Versilic.

A punch was used to cut out a cylinder 29 having a diameter of 8 millimeters and a height of 3 millimeters from a plate of carbon-filled silicone elastomer sold under the reference 9871D by Etablissements Garland. The cylinder 29 constituting the conducting material 10 was fitted in one end of the tube together with a fluoro-silicone sealing compound 30 sold under the reference CAF4 by Rhone Poulenc, and suitable for ensuring that the assembly is sealed and homogeneous. A sensitive membrane 31 was then deposited on the surface of the cylinder 29 made in the same way as described above in order to form a layer of ionically conductive material 9 delimiting the sensitive zone z.

This sensitive zone z was constituted by dissolving 2.5 mg of silicone sealing compound referenced Silastic A as sold by Dow Corning and 0.1 mg of a nonactin/monactin mixture in 20 µl of mesitylen. The resulting solution was deposited on the surface of the electrode with the solvent evaporating and polymerization taking place in air at ambient temperature.

Electrical continuity was obtained by means of an aluminum pin 32 implanted in the carbon-filled elastomer cylinder 29 and connected to a screened cable 33 which was held in place by a silicon elastomer grommet 34 placed at the other end of the tube.

The sensor made in this way was tested in a solution of 0.8 mol/l magnesium chloride having ammonium chloride dissolved therein at various concentrations lying in the range $10^{-5}$ mol/l to $10^{-1}$ mol/l.

Measurements were performed relative to a calomel reference electrode with both electrodes being connected to a high input impedance electronic NV-meter (Tacussel Aries 20,000).

The potentials stabilized completely after less than one minute of sensor immersion. The following results were obtained.

| Concentration of $HN_4^+$ | Measured Potential |
| --- | --- |
| 0 | 100.0 mV |
| $10^{-5}$ mol/l | 109.3 mV |
| $10^{-4}$ mol/l | 142.7 mV |
| $10^{-3}$ mol/l | 195.5 mV |
| $10^{-2}$ mol/l | 246.8 mV |
| $10^{-1}$ mol/l | 298.7 mv |

EXAMPLE 4

A pH measuring electrode, i.e. a selective electrode for $H^+$ ions was made using the method described in Example 3 and FIG. 6, using tridodecylamine as the ionic conductor 9 with an equal quantity of potassium tetrakis(p-chlorophenyl)borate salt associated therewith. This electrode was tested in solutions having a pH lying in the range 6.86 to 7.41, i.e. the range in which biological measurements are performed. The following results were obtained:

| pH | Potential on Day 1 | Potential on Day 4 |
| --- | --- | --- |
| 6.865 | 99.3 mV | 99.4 mV |
| 7.000 | 91.9 mV | 92.1 mV |
| 7.413 | 74.3 mV | 74.8 mV |

The slope of the response is noticeably less than Nernst's theoretical slope (about 80%), but the remarkable reproducibility of potentials over an interval of three days should be observed.

EXAMPLE 5

A sensor made in accordance with the method of Example 1 (FIG. 4) had its portion constituting the sensitive zone z renewed as follows.

The sensitive zone was abraded with 3M's P6000 type abrasive paper so as to completely remove the elastomer layer containing the ionically conductive filler sensitive to $K^+$ ions over a thickness of about 100 micrometers.

A layer 9 of ionically conductive material sensitive to calcium ions was then put in place using exactly the same procedure as described in Example 1 except that the ionic conductor or ionophore sensitive to calcium ions was constituted by 0.1 mg of W. Simon's substance ETH 1001 as sold by Fluka. An equal quantity of potassium tetrakis(p-chlorophenyl)borate (Fluka) was associated with this ionophore.

The new sensor obtained in this way was tested in $10^{-1}$ mol/l sodium chloride solutions containing calcium chloride in concentrations lying in the range $10^{-5}$ mol/l and $10^{-1}$ mol/l. Measuring conditions were identical to those described in Example 1.

The following results were obtained:

| Concentration of $Ca^{++}$ ions | Measured Potential |
|---|---|
| 0 | 75.8 mV |
| $10^{-5}$ mol/l | 81.9 mV |
| $10^{-4}$ mol/l | 102.2 mV |
| $10^{-3}$ mol/l | 130.8 mV |
| $10^{-2}$ mol/l | 159.0 mV |
| $10^{-1}$ mol/l | 194.2 mV |

This example shows that sensors in accordance with the present invention can be modified simply and cheaply.

EXAMPLE 6

Figures 7, 8:
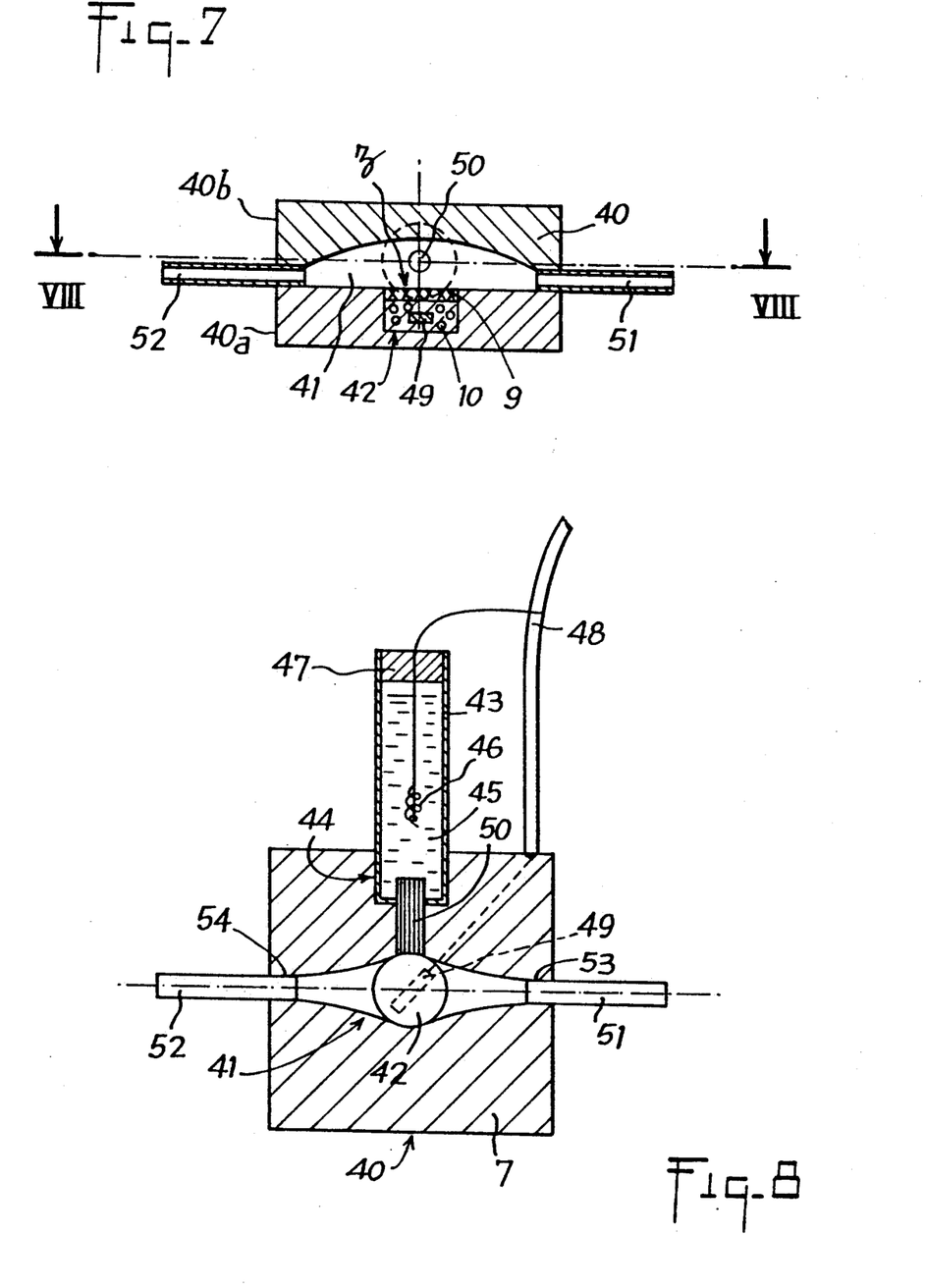
FIG. 7 is an elevation in section through another form of sensor in accordance with the invention.
FIG. 8 is a section taken substantially on line VIII—VIII of FIG. 7.

In the above examples, the sensor includes at least one active zone disposed in a face or a portion of a surface constituting a portion of the outside envelope of the sensor. This example relates to a sensor body of the type having an enclosed measurement chamber. Such a sensor, which is more specifically applicable to measuring the concentration of sodium ions in a flow of solution, is shown in FIGS. 7 and 8.

The body 40 is constituted by two plates 40a and 40b of Versilic silicon elastomer (sold by Vernerer) bonded together by CAF4 sealing compound (sold by Rhone Poulenc) and constituting the material of the matrix 7.

The plates 40a and 40b were hollowed out prior to assembly so that after being assembled they delimit a measurement chamber 41 into which a cavity 42 opens out, with said cavity being preferably formed in one of the plates. Before the plates were assembled, the cavity 42 was filled with a mass of carbon-filled elastomer as explained above in order to form the electronically conductive material 10, with said mass being covered with a layer of the type described in Example 3 using the ionophore compound ETH 227 (Fluka) as the ionic conductor 9 without associating a conductive salt therewith. The layer of material 9 thus defines a sensitive zone z in association with the chamber 41.

In this example, the reference electrode is integrated in the sensor and is constituted by a tube 43 of Versilic silicone elastomer (sold by Vernerer) inserted in an orifice 44 provided in the body 40 and sealed using CAF 4 sealing compound. Inside the tube 43, there is an aqueous solution 45 of 3 mol/l potassium chloride and a silver wire 46 electrically covered with a layer of silver chloride. The tube is closed by a silicone elastomer plug 47 with the chloride-coated silver wire 46 passing therethrough, and being soldered to the screen of a cable 48 which is also connected to a measuring apparatus and to a measuring electrode 49 constituted by a pin of aluminum inserted into the material 10 through the body 40. The liquid junction between the reference electrode and the measurement chamber 41 is provided by a rod of porous polyester 50 sold under the trademark Porex.

Finally, tubes 51 and 52 were inserted into the body 40 via holes 53 and 54 in order to allow the solution to be measured to enter and leave the chamber 41.

The sensor was used for measuring the concentration of sodium ions in aqueous solution, at concentrations lying between 50 mmol/l and 150 mol/l. The temperature was $25° C. \pm 1° C.$ The following results were obtained:

| Concentration (mmol/l) | Potential (mV) |
|---|---|
| 50 | 150.0 |
| 60 | 154.5 |
| 70 | 158.5 |
| 80 | 161.9 |
| 90 | 165.1 |
| 100 | 168.0 |
| 110 | 170.6 |
| 120 | 173.0 |
| 130 | 175.2 |
| 140 | 177.1 |
| 150 | 178.8 |

These results show that this sodium ion sensor can be used for metering sodium ions in biological samples (whole blood, serum, plasma) which contain concentrations of about 100 mmol/l.

EXAMPLE 7

On the lines of the method of Example 6, a double sensor has been made including an integrated reference electrode and capable of measuring the concentrations both of $K^+$ ions and of $Ca^{++}$ ions simultaneously on test samples having a volume of about 500 microliters. This sensor can also be used for continuous flow measurements.

Figure 9:
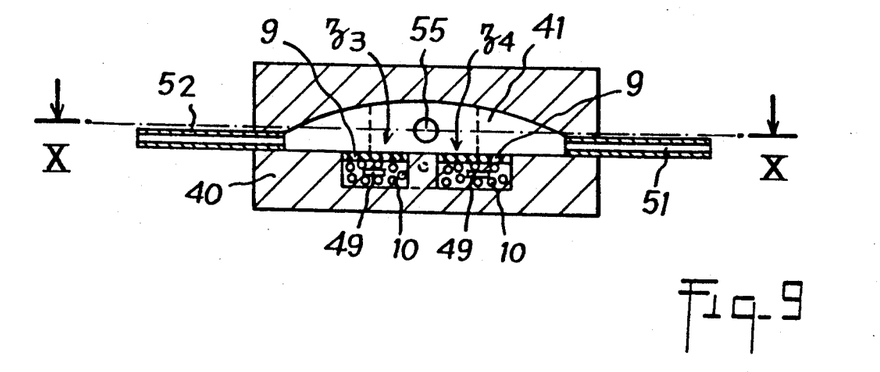
FIG. 9 is an elevation in section analogous to FIG. 7 showing an variant embodiment.
Figure 10:
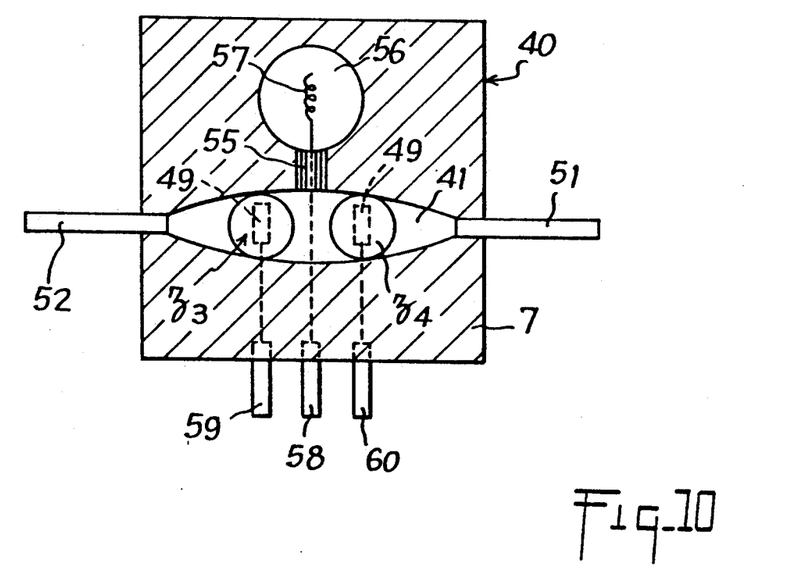
FIG. 10 is a section substantially on line X—X of FIG. 9.

Such a sensor, as shown in FIGS. 9 and 10, was made as described above in order to include two sensitive zones $z_3$ and $z_4$ which appear in the measurement chamber 41. The zone $z_3$ includes an ionic conductor material 9 responsive to $K^+$ ions, whereas the zone $z_4$ is sensitive to $Ca^{++}$ ions.

The measurement chamber 41 includes an orifice 55 providing a liquid connection with a compartment 56 containing a reference electrode. The compartment 56 is filled by means of a syringe with a 0.1 mol/l, solution of sodium chloride. A wire 57 of silver coated in silver chloride is immersed in the reference solution and is electrically connected to a connection pin 58 by means of a wire going through the body of the sensor.

The electrodes 49 for the zones $z_3$ and $z_4$ are connected to connection pins 59 and 60.

Tubes 51 and 52 serve respectively to insert and remove reference solutions and measurement solutions, either by continuous or by intermittent flow or else by means of a syringe installed in a tube which should then be made of a material capable of self-sealing. It is also possible to omit tubes 51 and 52 and insert the sampling and measurement liquids via a syringe fitted with a needle, in which case the silicone elastomer body acts as a self-sealing septum.

The above-described sensor has been tested under the following conditions.

Measurements were performed using an automatic millivoltmeter-ionmeter of the Ionoprocesseur (Tacussel) type having three measurement channels.

Measurement solutions were constituted by 0.1 mol/l sodium chloride having both potassium chloride and calcium chloride simultaneously dissolved therein at various concentrations lying in the range 1 mmol/l to 10 mmol/l.

The following results were obtained:

| Concentration of Potassium Ions | Measured Potential |
|---|---|
| 1 mmol/l | 173 mV |
| 3 mmol/l | 203 mV |
| 6 mmol/l | 221 mV |
| 10 mmol/l | 235 mv |

| Concentration of Calcium Ions | Measured Potential |
|---|---|
| 1 mmol/l | 57 mV |
| 3 mmol/l | 74 mV |
| 10 mmol/l | 91 mV |

Analysing the above examples shows that the invention can be used to provide homogeneous sensors which are cheap, sensitive, fast, and of any appropriate shape, which sensors can, in addition, be of a type suitable for plunging into the liquid or for placing against the liquid, or of the type having a cup for retaining the measurement solution, and/or of the multiple or the single type, which advantages have not been available in the prior art.

Possible interference from oxydo-reducing systems on the electrode of the invention has been tested.

To do this, an electrode was made using the method described in Example 1. This electrode was tested in two solutions A and B constituted as follows.

|  | Solution A (in mol/l) | Solution B (in mol/l) |
|---|---|---|
| Sodium chloride | 0.1 | 0.1 |
| Potassium hexacyanoferrate (III) Fe(CN)$_6$K$_3$ | $9 \times 10^{-5}$ | $2 \times 10^{-4}$ |
| Potassium hexacyanoferrate (II) Fe(CN)$_6$K$_4$ | $1.82 \times 10^{-4}$ | $1 \times 10^{-4}$ |

The person skilled in the art will really understand that the oxidizing and reducing species constituted by the following cations $[Fe(CN)_6]^{3-}$ and $[Fe(CN)_6]^{4-}$ are respectively at a ratio $\frac{1}{2}$ in solution A and at a ratio 2/1 in solution B, with the total concentration of $K^+$ ions being $10^{-3}$ mol/l in both cases.

The oxydo-reducing potentials of these solutions as measured using a platinum electrode are respectively 203.0 mV for solution A and 240.3 mV for solution B, giving a difference $\delta E$ of 37.3 mV as could be expected by application of Nerst's equation which predicts a value of $\delta E = 36$ mV.

Potential measurements performed using the protocol of Example 1 on both solutions gave the following results:

Solution A: 71.4 mV
Solution B: 73.2 mV

This test shows that the interference from oxydo-reducing systems is practically negligible with an electrode of the invention whereas in the prior art, as described in particular by the publication "Solid contact in membrane ion selective electrode" in "Ion Selective Electrodes Review", 1985, vol. 7, page 25, it is known that solid contact selective electrodes have an appreciable response to oxydo-reducing systems.

Sensors in accordance with the invention have been tested in comparison with the solid type electrodes of Lima and Machado as mentioned above.

The tests were performed using two sensors of the present invention made in accordance with FIG. 3 and in comparison with two Lima and Machado electrodes.

The electrodes of the invention were made using Example 1. As shown in FIG. 11, the Lima and Machado electrodes comprised a body 7 of polymethylmethacrylate (registered trademark Plexiglas) surrounding a silver conductor 71 connected to a cable 72. The conductor 71 projects into a housing 73 provided at the free end of the body 70 and filled with a mixture 74 of silver-filled epoxy resin.

The end of each Lima-Machado electrode was covered with a layer of PVC including an ionophore such as valinomycin. The PVC layer was applied to the end of the electrode by dipping into a solution comprising 15 mg of valinomycin, 0.33 g of dioctyle adipate, and 0.24 g of granulated PVC in about 10 ml of tetrahydrofuran. A first Lima-Machado electrode (1) was dipped once into the solution and the layer adherring thereto was allowed to dry in air for 24 hours. A second Lima-Machado electrode (2) was dipped twice into the solution and allowed to dry in air for 24 hours. The PVC layers were 10 μm and 20 μm thick, respectively.

A recess was made in the mixture 74 of the second LimaMachado electrode (2) in order to receive the sensitive membrane solution. The solution was deposited so as to impart a thickness of about 100 μm to the membrane.

The electrode was again allowed to dry for 24 hours at ambient temperature in order to evaporate the tetrahydrofuran.

The four electrodes were used for preliminary test purposes in $10^{-3}$ mol/l to $10^{-1}$ mol/l solutions of potassium chloride in the presence of a 0.1 mol/l NaCl support electrolyte for about one day in order to ensure they were properly prepared.

After washing and wiping, the electrodes were subjected to long term drift testing. To this end, the electrodes were immersed in a solution of $10^{-3}$ mol/l KCl and 0.1 mol/l NaCl disposed in a receptacle and maintained at a temperature of 25° C. by a bath of water. The potentials of the electrodes were measured relative to a Radiometer reference K 701 reference electrode, 4 mol/l Hg/hg$_2$Cl$_2$/saturated KCl/HCOONa.

The observed drift and respective potentials are given in following Tables I and II.

TABLE I

| Duration in Hours | Potential in mV | | | |
|---|---|---|---|---|
|  | Sensor in Accordance with the Invention | | Lima-Machado Electrodes | |
|  | 1 | 2 | 1 | 2 |
| 0 | 136.6 | −48.3 | 90.9 | 85.6 |
| 2 | 149.1 | −41.3 | 63.9 | 62.0 |
| 64 | 167.2 | −24.9 | 18.7 | −16.0 |
| 87 | sensor failure | −21.3 | 12.5 | electrode failure |

TABLE II

| Duration in Hours | Drift in mV/Hour | | | |
|---|---|---|---|---|
|  | Sensor in Accordance with the Invention | | Lima-Machado Electrodes | |
|  | 1 | 2 | 1 | 2 |
| 0–2 | 6.3 | 3.5 | 13.5 | 6.8 |
| 2–64 | 0.3 | 0.26 | 0.78 | 1.42 |
| 64–87 | — | 0.16 | 0.27 | — |

Although both types of electrodes show up drift in potential, it may be observed that sensors in accordance with the invention are objectively better than Lima-Machado electrodes in this respect.

The invention is not limited to the examples described and shown, since numerous modifications may be made without going beyond the scope of the invention.

I claim:

1. A homogeneous potentiometer sensor for sensing the presence of ions in a measurement solution, the sensor comprising a body having at least one active surface portion or face delimiting at least one zone which is sensitive to an ionic species, the sensor being provided with a conductor of an electrically conductive material disposed in relationship to the body and connected to an electrical connection cable, wherein:

the body is a matrix body made of a single material which does not conduct electricity, which is chemically inert, and which has the ability to be filled with various different materials in the dispersed, dissolved, or grafted state;

the sensitive zone of the matrix body comprises:

a layer or thickness of ion sensitive material dispersed, dissolved, or grafted into the matrix body for being put into contact with the measurement solution;

an underlayer or underthickenss of an electronically conductive material dispersed, dissolved, or grafted into the matrix body; and an intermediate layer or thickness in intimate connection with the layer and with the underlayer and which is dispersed, dissolved, or grafted into the matrix body; and the conductor passes through a portion of the matrix body in sealed manner and is inserted into the underlayer.

2. A sensor according to claim 1 wherein the body is made of a material selected from polymers.

3. A sensor according to claim 1, wherein the body is made of a material selected from elastomers.

4. A sensor according to claim 1, wherein the body includes an active surface portion or face constituting a portion of an external envelope of the body.

5. A sensor according to claim 1 wherein the body includes an active surface portion or face forming a portion of a chamber delimited by the body.

6. A sensor according to claim 5, wherein the chamber is associated with tubes for con a flow circuit for the measurement solution.

7. A sensor according to claim 5, wherein the chamber includes at least one tube made of a material which is self-sealing when punctured by syringe needles.

8. A sensor according to claim 1, wherein the body includes an active surface portion or face delimiting a set-back portion including at least one sensitive zone and providing a small cup relative to the surface portion or face suitable for retaining a quantity of measurement solution.

9. A sensor according to claim 1, wherein a reference electrode is disposed in a compartment delimited by the body in contacting relationship with the measurement solution.

10. A sensor according to claim 1, wherein the body includes at least two same-sensitivity zones separate from one another.

11. A sensor according to claim 1 wherein the body includes at least two zones of different sensitivities.

12. A sensor according to claim 1, wherein said layer of an ion sensitive material is flush with said active face of said sensitive zone, and wherein said underlayer of electronic conductive material is at a depth inside the body and at a distance from said active face.

13. A sensor according to claim 12, wherein the layer of ion sensitive material is not less than one millimeter thick.

14. A sensor according to claim 13, wherein the layer or thickness of an ion sensitive material also includes an organic salt.

15. A sensor according to claim 12, wherein the electronically conductive material is not less than one micrometer thick.

16. A sensor according to claim 15, wherein the electronically conductive material has a grain size which is preferably less than 5 micrometers.

17. A sensor according to claim 1, wherein the conductor is a piece of semiconductor material.

18. A sensor according to claim 17, wherein the conductor is a piece of monocrystalline silicon.

* * * * *